US011160862B2

(12) United States Patent
Huang et al.

(10) Patent No.: US 11,160,862 B2
(45) Date of Patent: Nov. 2, 2021

(54) NANOEMULSION ADJUVANT FOR NASAL MUCOSA AND PREPARATION METHOD THEREOF

(71) Applicant: NATIONAL HEALTH RESEARCH INSTITUTES, Zhunan Town (TW)

(72) Inventors: Ming-Hsi Huang, Zhunan Town (TW); Chung-Hsiung Huang, Zhunan Town (TW); Chiung-Yi Huang, Zhunan Town (TW)

(73) Assignee: NATIONAL HEALTH RESEARCH INSTITUTES, Zhunan Township, Miaoli County (TW)

(*) Notice: Subject to any disclaimer, the term of this patent is extended or adjusted under 35 U.S.C. 154(b) by 168 days.

(21) Appl. No.: 16/172,207

(22) Filed: Oct. 26, 2018

(65) Prior Publication Data
US 2019/0125863 A1    May 2, 2019

(30) Foreign Application Priority Data
Oct. 27, 2017 (TW) .................... 106137133

(51) Int. Cl.
*A61K 39/39* (2006.01)
*A61K 39/00* (2006.01)
*A61P 35/00* (2006.01)

(52) U.S. Cl.
CPC ............... *A61K 39/39* (2013.01); *A61P 35/00* (2018.01); *A61K 2039/543* (2013.01); *A61K 2039/55566* (2013.01); *A61K 2039/585* (2013.01)

(58) Field of Classification Search
None
See application file for complete search history.

(56) References Cited

U.S. PATENT DOCUMENTS

2009/0324727 A1* 12/2009 Foguet Roca ......... A61K 8/375
424/489
2011/0052633 A1*  3/2011 Huang .................... A61P 37/04
424/209.1

\* cited by examiner

Primary Examiner — Trevor Love
(74) Attorney, Agent, or Firm — Muncy, Geissler, Olds & Lowe, P.C.

(57) ABSTRACT

The invention provides a nanoemulsion adjuvant and a preparation method thereof, which are composed of the following components: a continuous aqueous phase containing $H_2O$ molecules, an oil phase material containing fats and oils, and an emulsion system for stabilizing the interface between the continuous aqueous phase and the oil phase, and the emulsion system is an emulsifier mixture. The adjuvant is characterized in that the emulsion system does not contain an ionic emulsifier and the particle size of the emulsion is between 20 and 200 nanometers. The use of the nanoemulsion adjuvant can prevent toxicity and possible harm of ionic emulsifiers to human cells, and provide a vaccine preparation capable of eliciting a high degree of immune response.

13 Claims, 7 Drawing Sheets

NANOEMULSION ADJUVANT FOR NASAL MUCOSA AND PREPARATION METHOD THEREOF

CROSS-REFERENCE TO RELATED APPLICATION

BACKGROUND OF THE INVENTION

Technical Field of the Invention

The present invention relates to an immunity adjuvant and a preparation method thereof, and more specifically to a nanoemulsion adjuvant and a preparation method thereof, which is accompanied by an antigen and administered through the nasal mucosa, can enhance the immune titer of an antigen.

Background

Emulsions are a type of dispersed system that is widely used in pharmaceutical formulations. Its use is to disperse solid drugs that are not easily soluble in water or liquid drugs that are immiscible with water in the form of fine droplets in a medium for drug delivery. Emulsions are mainly composed of an internal phase and an external or continuous phase, and are classified into different emulsion types according to different internal and external phase compositions, including an aqueous phase solution as an internal phase and an oil phase solution as continuous phase (water-in-oil, W/O), oil phase solution as internal phase and aqueous phase solution as continuous phase (oil-in-water, O/W) and oil phase solution coating the aqueous phase was used as the internal phase and the aqueous phase as the continuous phase (water-in-oil-in-water, W/O/W). Emulsions are administered in a variety of routes, including subcutaneous, intramuscular, transdermal, or mucosal administration. Among them, the emulsion used for mucosal administration is the main topic of emulsion development in recent years.

The nasal cavity and the oral cavity have a large area of mucous membranes and are distributed with quite dense micro-vessels. Compared to other human drug delivery routes, which have biological barriers that are difficult for drugs to penetrate, drugs are administered through densely distributed microvessels in mucosal tissue can not only be quickly absorbed into the human blood system to speed up the onset time after drug administration, but also can prevent the drug from being degraded by the enzymes of the gastrointestinal tract or being inactivated metabolically when passes through the intestinal mucosa and liver, thereby improving the bioavailability of the drug. On the other hand, due to the dense distribution of microvessels in mucosal tissues, this is the region where the immune system response occurs most frequently and is the main site for localized specific immune responses. Therefore, mucosal immunity plays an important role in the immune system and is the first barrier for organisms to resist the invasion of pathogens. For the reason, more and more immune preparations use mucosal tissue as the subject of the administration.

In recent years, the development of pharmaceutical compositions via mucosal tissues has progressed steadily. In general, effective stimulation of the immune system by the antigen is necessary for the vaccine to evoke effective immunity. However, more appropriate mucosal immunological carriers or adjuvants are still required for mucosal administration. For example, the small-sized emulsion particles prepared by the cationic emulsifier is a non-viral gene carrier with great development potential, which can be assembled with DNA, antigens, antibodies, proteins, or other small molecules in solution to form complexes with the same particle size. This small-sized complex is easier to pass through the cell membrane, its charge characteristics make it easier to get close to the negatively charged cell membrane and is taken up by the cells, and provide good drug stability so that the ingredient will not be destroyed in the body before reaching the target tissue.

The challenge when emulsions are applied to adjuvants is that the emulsifier used to balance the oil and water phases in the emulsion can be metabolized and not harmful to the human body. Most of the adjuvants prepared in the prior art use ionic emulsifiers, which increase the metabolic burden on the human body. On the other hand, membrane glycoproteins in antigens are exposed to ionic emulsifiers for a long time, which may lead to denaturation.

On the other hand, there are also several difficulties in the preparation of non-ionic emulsions with small particle sizes that must be overcome. Since the hydrophilicity of its hydrophilic group is weak, it is necessary to increase the amount of hydrophilic groups to make the entire molecule water-soluble. In addition, most of the lipophilic groups or hydrophilic groups in the disperse system are charged, but the non-ionic emulsifiers do not ionize in the solution system and do not form an adsorption layer around the dispersed phase. In addition, most of the lipophilic groups or hydrophilic groups in the disperse system are charged, and the non-ionic emulsifiers are not ionized in the solution system, so that an adsorption layer cannot be formed around the dispersed phase. Its ability to stabilize solution systems is insufficient compared to the general ionic emulsifiers. At the present stage, the preparation of small particle size emulsions is still mainly based on mixing of aqueous liquids and oily liquids followed by homogenization. The emulsion obtained by the above preparation method has a particle size of about micron to submicron, and besides the inability to provide finer particles, the stability of the overall dispersion system is also insufficient.

Therefore, the design of a nanoemulsion adjuvant, which can efficiently induce immune responses in the nasal mucosa, does not increase the metabolic burden on the human body, promotes immune effects and increases drug delivery efficiency, and has become a issue that needs to be solved in related fields. Therefore, designing a nanoemulsion adjuvant capable of efficiently eliciting an immune response in the nasal mucosa without increasing the metabolic burden on the human body and improving drug delivery is an important issue in related fields.

SUMMARY OF INVENTION

The main object of the present invention is to provide a nanoemulsion adjuvant, which does not contain ionic emulsifiers and does not cause severe reactions to human body. And providing a vaccine formulation for nasal mucosal vaccination that induces a high degree of immune response by using the antigen with the adjuvant together.

It is still a further object of the present invention to provide a nanoemulsion adjuvant, especially forming a tumor vaccine by mixing the tumor antigen with the adjuvant together which is able to inhibit tumor growth.

It is also an object of the present invention is to provide a nanoemulsion adjuvant and a preparation method thereof. By this method, a nanoscale emulsion containing a highly homogeneous nano-lipid particle can be efficiently and stably prepared, and the particle size of the nano-lipid particle can be controlled In order to achieve the above objects, the present invention discloses a nanoemulsion adjuvant, which is capable of enhancing the immune titer of an antigen accompanied by the administration of the antigen through the nasal mucosa, and is composed of a continuous aqueous phase containing $H_2O$ molecules, an oil phase containing metabolizable oil and an emulsion system for stabilizing the continuous aqueous and oil phase interfaces and consisting of an emulsifier mixture, wherein the emulsion system does not contain an ionic emulsifier, and the particle size of the emulsion is between 20 and 200 nanometers.

In an embodiment of the present invention, it is also disclosed that the composition of the nanoemulsion adjuvant does not contain an immunostimulating substance, including a Toll-like receptor (TLR) agonist or a short antibacterial peptide, such as CpG oligodeoxynucleotides (TLR-9), host defense peptide (TLR-4), saponins (TLR-2, TLR-4), monophosphoryl lipid A (TLR-4), flagellin (TLR-5).

In an embodiment of the present invention, it is also disclosed that the emulsion system does not contain a cationic emulsifier, and the cationic emulsifier contains cetylpyridinium halides, cetylpyridinium chloride, cetyltrimethylammonium halides, cetyldimethylethylammonium halides, cetyldimethylbenzylammonium halides, cetyltributylphosphonium halides, dodecyltrimethylammonium halides and tetradecyltrimethylammonium halides.

In an embodiment of the present invention, it is also disclosed that the continuous aqueous phase is a pure aqueous solution, a phosphate solution, a citrate solution, a carbonate solution, a bicarbonate solution, a potassium chloride solution, a sodium chloride solution, a glucose solution or a lactated Ringer's solution.

In an embodiment of the present invention, it is also disclosed that the oil phase is a body-metabolizable lipid or fatty acid.

In an embodiment of the present invention, it is also disclosed that the body metabolizable lipid is one selected from the group consisting of animal oils, vegetable oils, natural oils, synthetic oils, and semi-synthetic derivatives, or any combination thereof.

In an embodiment of the present invention, it is also disclosed that the oil phase solution is at least one aqueous simple emulsion droplet further dispersed in an oil phase solution or an oil shell formed by the oil phase solution to form a multiple emulsion.

In an embodiment of the present invention, it is also disclosed that the composition comprises: greater than 99% by weight of a continuous aqueous phase, less than 1° % by weight of an oil phase material, and between 0.01% and 0.2° % by weight of a emulsion system.

In order to achieve the above objects, the present invention also discloses a method for preparing a nanoemulsion, which can increase the immune titers of the antigen. The method comprises the following steps: an emulsifier of emulsion system is dissolved in the first aqueous solution to obtain the first aqueous mixture; an emulsifier of emulsion system is dissolved in the oil phase solution to obtain the oil phase mixture; Mixing the first aqueous phase mixture with the oil phase mixture to obtain an oil-water mixture; the oil-water mixture is homogenized to form a storage solution; the stock solution is diluted with a second aqueous solution to form a dilute solution; The dilute solution is pressurized through a membrane having a specific nanometer pore size to obtain a nanoscale emulsion.

In an embodiment of the present invention, the step of pressing the solution through the membrane is also disclosed. The membrane having the selected nanopores is disposed in the middle of a bidirectional pressing device so that the bidirectional pressing device is divided into two sides. When the dilute solution is pressed from one side of the bidirectional pressing device through the membrane to the other side, the dilute solution can be pressed from the other side of the bidirectional pressing device through the membrane back to the original side.

In an embodiment of the present invention, it is also disclosed that the step of pressing through membrane back and forth is repeated at least once until the size of the emulsion particles in the diluted solution is the same as the pore size of the membrane, and the size distribution is uniform.

In an embodiment of the present invention, it is also disclosed that after the step of pressing through membrane, the membrane is replaced with another membrane having smaller pores, and the step of pressing through the membrane is repeated.

In an embodiment of the present invention, it is also disclosed that the bidirectional pressing device is a standard extruder used for preparing a liposome.

BRIEF DESCRIPTION OF THE DRAWINGS

The color figure (FIG. 7) is necessary for clearly recognizing the technical content and inventive spirit provided by the present invention. Hereby declare.

DETAILED DESCRIPTION OF THE INVENTION

Figure 1:
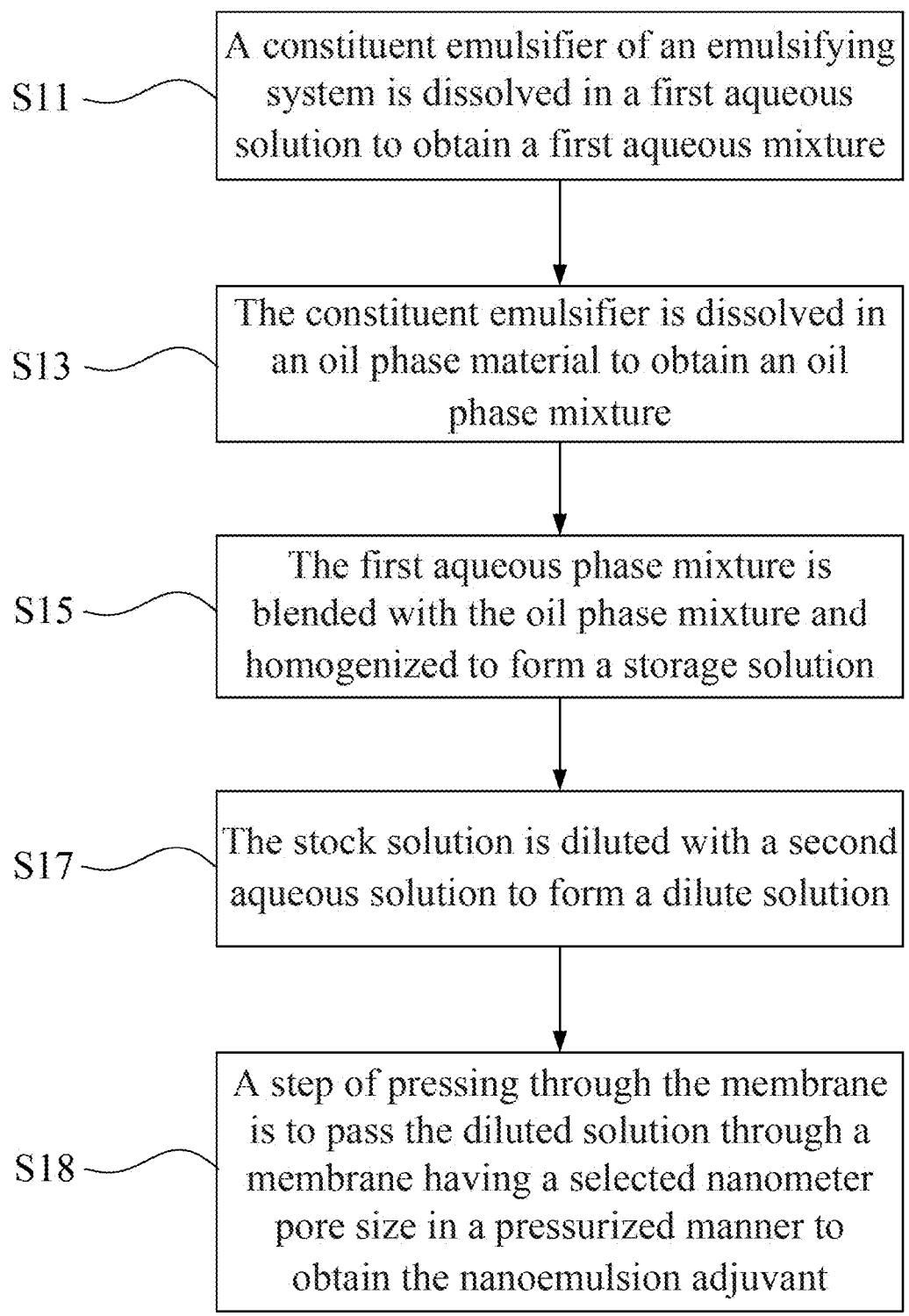
FIG. 1. A flow chart of a method for preparing a nanoemulsion according to a preferred embodiment of the present invention.

The terms used in this specification generally have their intended meaning in the technical field, the scope of the present invention, and a specific situation. The following description and some of the terms used elsewhere in this specification will allow the operator to further understand the present invention. The examples discussed in this specification and the terms used are for illustrative purposes only and are not intended to limit the scope or meaning of the present invention. Similarly, the present invention is not limited to the embodiments described in this specification.

All technical and scientific terms used herein, unless specifically stated otherwise, have the same meaning as commonly understood by one of skill in the art. In the event of a conflict in meaning, this specification shall prevail.

The term "emulsifier composition" as used herein refers to a substance having a structure of a hydrophilic tip and a lipophilic tail. When one end is close to the water phase and the other end is close to the oil phase, it can be located at the junction of the two phases. The physicochemical properties of the overall solution phase are stabilized by reducing the surface tension.

The term "ionic emulsifier" as used herein refer to a type of emulsifiers that dissociate in water to produce positive or negative hydrophilic ion groups, which can reduce the surface tension to stabilize the overall solution phase.

The term "non-ionic emulsifier" as used herein refer to a type of emulsifiers that does not dissociate in water. Among such emulsifiers, reducing the surface tension to stabilize the overall solution phase is not by a ionic functional group.

The term "biodegradable" as used herein, generally refers to macromolecular polymers that are degraded and dispersed in the body (this definition excludes environmental, fungal, or bacterial degradation). Biodegradable polymers may be attacked by biomolecules to affect the integrity of their systems, breaking down into fragments or other by-products of degradation. The resulting fragments may leave the site of action but do not necessarily disappear in the body.

The term "bioresorbable" as used herein, generally means that the polymer bulk is degraded and further absorbed within the body, that is, the polymer's by-products of degradation can be eliminated by metabolic pathways. bioresorption thus reflects the concept of bulk degradation of foreign bodies and by-products (low molecular compounds) in the absence of side effects, and completely eliminated.

The term "Bioactive agent" as used herein comprise a immunostimulant that induces activation or increases activity of any composition to stimulate immune system.

Most of the emulsion adjuvant in the prior art use an ionic emulsifier, resulting in an increase in the metabolic burden on the human body and may cause other adverse reactions. The present invention provides a non-ionic emulsifier nanoemulsion adjuvant. The ability of non-ionic emulsifiers to stabilize solution systems is weaker than that of ionic emulsifiers, making it difficult to prepare nanoemulsions. The present invention also provides a novel preparation method to provide a nanoemulsion adjuvant with high induction of immune response and no adverse effects on human body.

Therefore, the present invention provides a nanoemulsion adjuvant and a preparation method thereof, wherein the emulsion system does not contain an ionic emulsifier. The suspension is passed through a membrane having a nanometer pore size in an external pressurizing manner, so that the particle size of the lipid particles of the suspension can be adjusted according to the pore diameter of the membrane, thereby overcoming the submicrometer level limit when treated by ultrasonic vibration or homogenizer homogenization, and give more uniform nano-lipid particles, improve the quality of nanoemulsion formulations and drug delivery efficiency.

Based on the above guidelines, the following describes the materials, material properties and preparation methods of the nanoemulsion adjuvant provided by the present invention:

This present invention provides a nanoemulsion adjuvant, which is capable of enhancing the immune titer of an antigen accompanied by the administration of the antigen through the nasal mucosa, and is composed of a continuous aqueous phase containing H2O molecules, an oil phase containing lipid and an emulsion system for stabilizing the continuous aqueous and oil phase interfaces and consisting of an emulsifier mixture, wherein the emulsion system does not contain an ionic emulsifier, and the particle size of the emulsion is between 20 and 200 nanometers.

In a preferred embodiment, the composition of the nanoemulsion adjuvant comprises: greater than 99% by weight of a continuous aqueous phase, less than 1% by weight of an oil phase material, and between 0.01% and 0.2% by weight of a emulsion system.

Wherein, the continuous aqueous phase is used to disperse the dispersible medium therein. The dispersible medium includes a soluble compound, an oil phase material, or any material embedded in an oil phase solution. The first aqueous solution provided by the present invention may be a pure aqueous solution or an aqueous compound solution. Wherein, in a preferred embodiment, the aqueous solution can be prepared from a phosphate compound, a citrate compound, a (bi)carbonate compound, potassium chloride, sodium chloride, or various medical infusion such as a glucose aqueous solution, a lactated Ringer's solution.

Wherein, the oil phase material is a dispersed phase in the emulsion system, is a medically acceptable oily material, and in order to enable the nanoemulsion adjuvant to smoothly perform pharmacological actions in the body, in a preferred embodiment, the oil phase material is a metabolizable oil or fatty acid. The oil phase material provided by the present invention is selected from one of the group consisting of animal oils, vegetable oils, natural oils, synthetic oils, and semi-synthetic derivatives, or any combination thereof.

Wherein, the emulsion system is composed of an emulsifying agent composition, which is used to make the oil and water phases miscible with each other to form a uniform dispersion or emulsion. The emulsifier must be selected to be compatible with the other ingredients in the emulsion and does not affect the stability and effectiveness of the related substances. In the nanoemulsion adjuvant provided by the present invention, the emulsifying agent composition stabilizes the oil phase material in the continuous aqueous phase, so that generally higher hydrophilicity is required, and the hydrophilic-lipophilic balance (HLB) of hydrophilic emulsifying agent is between 8 and 18. Based on the above principles, emulsifier provided in the present invention can be selected from the group consisting of volvoxvlropylene mannitoldioleate, polyoxyethylene sorbitol lanolin oleate derivative, polyoxyethylene sorbitol lanolin derivative, polyoxypropylene stearate, polyoxyethylene(5EO) lanolin alcohol, sorbitan monolaurate, polyoxyethylene fatty acid, polyoxyethylene oxypropylene oleate, polyoxyethylene sorbitol beeswax derivative, tetraethylene glycol monolaurate, polyoxyethylene lauryl ether, polyoxethylene(4EO) sorbitan monostearate, Hexaethylene glycol monostearate, polyoxypropylene(5PO) laolin alcohol, polyoxyethylene(5EO) sorbitan monooleate, polyoxyethylene esters of mixed fatty and resin acids, polyoxyethylene cetyl ether, polyoxyethylene (20EO) sorbitan tristearate, polyoxyethylene(20EO) sorbitan tribleate, polyoxyethylene lanolin derivative, polyoxyethylene monooleate, polyoxyethylene monolaurate, polyoxyethylene monopalmitate, polyoxyethylene monostearate, polyoxyethylene(10EO) oleyl alcohol, polyoxyethylene alkyl phenol, acetylated polyoxyethylene(10EO) lanolin derivative, polyoxyethylene alkyl aryl ether, polyoxyethylene castor oil, polyoxyethylene vegetable Oil, polyoxyethylene(4EO) sorbitan monolaurate, polyoxyethylene(24EO)

cholesterol, polyoxypropylene(20PO) lanolin alcohol, polyoxyethylene sorbitan monolaurate, polyoxyethylene(20EO) sorbitan monostearate, polyoxyethylene(20EO) oleyl alcohol, polyoxyethylene(20EO) methyl glucoside sesquistearate, polyoxyethylene(16EO) lanolin alcohol, polyoxyethylene(25EO) lanolin alcohol, acetylated polyoxyethylene (9EO) lanolin derivative, polyoxyethylene(20EO) sorbitan monooleate, polyoxyethylene oleyl ether, polyoxyethylene stearyl alcohol, polyoxyethylene oleyl alcohol, polyoxyethylene fatty alcohol, polyoxyethylene glycol monopalmitate, polyoxyethylene(20EO) sorbitan monopalmitate, polyoxyethylene cetyl alcohol, polyoxyethylene oxypropylene stearate, polyoxyethylene(20EO) sorbitan monolaurate, sodium oleate, mannide fatty acid ester, sorbitan fatty acid ester, polyoxyethylene sorbitan fatty acid ester, poly(ethylene glycol)/poly(lactide-ε-caprolactone) block copolymer and poly (ethylene glycol)/poly(L-lactide) block copolymer or any combination thereof.

On the other hand, the nanoemulsion adjuvant provided by the present invention is different from the emulsion immunity adjuvant of the prior art in that it uses only a non-ionic emulsifier as a material to stabilize the solution system. By providing a nanoemulsion adjuvant using only a non-ionic emulsifier as an emulsification system, it is less biotoxic than other ionic emulsifiers when delivered to an organism. Although the overall preparation is more difficult, it is a safer choice for emulsifier in drug delivery.

In a preferred embodiment of the present invention, the emulsification system is free of a cationic emulsifier, and the cationic emulsifier comprises cetylpyridinium halides, cetylpyridinium chloride, cetyltrimethylammonium halides, cetyldimethylethylammonium halides, cetyldimethylbenzylammonium halides, cetyltributylphosphonium halides, dodecyltrimethylammonium halides, tetradecyltrimethylammonium halides.

In general, the nonionic emulsifier has a pH of from 3 to 10, and exists as a neutral molecular or micelle when dissolved in water or an organic solvent, and thus is stable in acidic, alkaline and electrolyte solutions without causing precipitation. Based on the above principles, the nonionic emulsifier may be a polyoxyethylene or polyol. In a preferred embodiment, the nonionic emulsifier is selected from the group consisting of polyoxyethylene sorbitan carboxylic esters, poly(ethylene glycol)-block-poly(lactide-ε-caprolactone) copolymer, poly(ethylene glycol)-block-poly(lactic acid) copolymer, mannide fatty acid ester, sorbitan fatty acid ester, sorbitan-poly(lactide-co-ε-caprolactone) copolymer, coconut oil reducing alcohol, cetyl alcohol, oleyl alcohol, glycerin, pentaerythritol, nonylphenol, octylphenol, octylcresol, sorbitol, ethanolamine, isopropanolamine, sucrose, lauric acid, coconut oil fatty acid, tetradecanoic acid, palmitic acid, Oleic acid, Stearic acid or any combination thereof.

In the nanoemulsion adjuvant provided by the present invention, the particle size of the particles in the emulsion is an important key for the efficient administration of the emulsion immunoadjuvant in the nasal cavity. Nanoparticles within the emulsion system can be rapidly administered in the nasal cavity where dense microvessels are distributed to accelerate the onset of action after drug administration. At the same time, when DNA, antigens, antibodies, proteins, or other small molecules are assembled with small-particle-size emulsions to form a complex with a small particle size, they are more easily taken up by the cell membrane. Furthermore, the charge it carries can be attracted to negatively charged cell membranes, making it easier for the complexes to be taken up by the cell membranes, and providing sufficient drug stability to prevent the components from suffering damage before reaching the target tissue. Furthermore, the charged complexes can be attracted to negatively charged cell membranes, are more easily accessible to the cell, and provide sufficient drug stability to prevent the components from being destroyed in vivo before reaching the target tissue. Based on the foregoing, the particles of the nanoemulsion adjuvant provided by the present invention have a particle size of between 20 and 200 nanometers.

Further, in a preferred embodiment of the present invention, the nanoemulsion adjuvant provided by the present invention has a high administration efficiency, and is easily taken up by cells through cell membranes, and provides sufficient drug stability to avoid antigens from being destroyed in vivo before reaching the target tissue. Therefore, the nanoemulsion adjuvant provided by the present invention does not have to be used in conjunction with other bioactive agents, wherein the bioactive agent comprises an immunostimulant that stimulates the immune system by inducing activation or increasing the activity of any of the components of the composition (drugs and nutrients). For example, the type of immune stimulant not possessed by the nanoemulsion adjuvant provided by the present invention includes, but is not limited to, a toll-like receptor (TLR) agonist or a short antibacterial peptide, such as CpG oligodeoxynucleotide (TLR-9), saponin (TLR-2, TLR-4), monophosphoryl lipid A (TLR-4), flagellin (TLR-5), and antibacterial peptide (TLR-4).

On the other hand, in a preferred embodiment of the present invention, the oil phase material may further have at least one aqueous simple emulsion droplet dispersed in the continuous aqueous phase or the oil shell formed by the continuous aqueous phase to form a multiple emulsion. Wherein, the solution system needs to contain a lipophilic emulsifier stably combined with the aqueous phase and the oil phase, so that the aqueous phase simple emulsion droplets can stably present in the continuous aqueous phase or the oil shell formed therefrom. The hydrophilic lipophilic balance (HLB) of the lipophilic emulsifier is between 1 and 7, preferably 3 to 6. Based on the foregoing principles, in a preferred embodiment of the present invention, Based on the foregoing principles, in a preferred embodiment of the present invention, the lipophilic emulsifier is selected from the group consisting of mannide fatty acid esters, sorbitan fatty acid esters, sorbitan-poly(lactide-ε-caprolactone) copolymer, and sorbitan-poly(lactic acid) copolymer or any combination thereof. Through this design of the emulsion with aqueous simple emulsion droplets, the release of the loaded components can be control more precisely. On the other hand, when the emulsion is used as a carrier of a vaccine, it can elevate the body's response to the immunogen and/or effectively induce the activation of the antigen-presenting cells.

Hereinafter, the materials used for the nanoemulsion adjuvant provided by the present invention, material properties, and the preparation method thereof will be further described:

Please refer to FIG. 1 of the present invention, which is a flow chart of a method for preparing a nanoemulsion adjuvant according to an embodiment of the present invention. As shown in the figure, the preparation method of the nanoemulsion adjuvant is as follows:

S11: A constituent emulsifier of an emulsifying system is dissolved in a first aqueous solution to obtain a first aqueous mixture;

S13: The constituent emulsifier is dissolved in an oil phase material to obtain an oil phase mixture;

S15: The first aqueous phase mixture is blended with the oil phase mixture and homogenized to form a storage solution;

S17: The stock solution is diluted with a second aqueous solution to form a dilute solution S18: A step of pressing through the membrane is to pass the diluted solution through a membrane having a selected nanometer pore size in a pressurized manner to obtain the nanoemulsion adjuvant.

As shown in the step S11, the method for preparing the nanoemulsion provided in a preferred embodiment of the present invention comprises that A constituent emulsifier of an emulsifying system is dissolved in a first aqueous solution to obtain a first aqueous mixture.

Wherein, the first aqueous phase solution is a continuous aqueous phase in the whole nanoemulsion for dispersing the dispersible medium in the continuous aqueous system. The Emulsifying Agents are used to immiscible oil phase and water phase, so that the solution forms a uniform dispersion or emulsion. The definition and properties of the emulsifying agents and the first aqueous solution have been described in the composition of the nanoemulsion adjuvant described above and will not be described here.

In another aspect, the invention provides a method for preparing a nanoemulsion adjuvant, which uses only a non-ionic emulsifying agent to stabilize the solution system. When delivered to an organism, it has lower biological toxicity than other ionic emulsifying agents. Therefore, it is an emulsifier choice that is more difficult to operate but safer in drug delivery use. The definition and properties of the non-ionic emulsifying agents have been described in the composition of the nanoemulsion adjuvant described above and will not be described here.

As shown in the steps of S13 and S15, an oil phase material is further added to the first aqueous phase mixture of step S11 and mixed to form an oil phase mixture. In order to uniformly distribute the oil phase material in the nanoemulsion, in an embodiment, an external force is further applied to the mixed solution. The emulsifier in the aqueous phase solution can reduce the surface tension between the oil phase and the water phase, so that the oil phase material is contoured with the emulsifier and the aqueous phase solution after being dissipated by the external force, so that the oil phase material is stably distributed in the emulsion system. As the external force applied is stronger, the oil phase solution will be split up into smaller units, and will be more evenly dispersed in the nanoemulsion adjuvant to form a highly homogeneous and uniform stock solution.

Wherein, the oil phase material is a pharmaceutically acceptable oily substance, so that the nanoemulsion adjuvant can smoothly perform pharmacological actions in the body. On the other hand, in a preferred embodiment of the present invention, the oil phase material may further have at least one aqueous simple emulsion droplet dispersed in the continuous aqueous phase or the oil shell formed by the continuous aqueous phase to form a multiple emulsion. Wherein, the definition and properties of the oil phase material and the multiple emulsion have been described in the composition of the nanoemulsion adjuvant described above, and will not be described here.

When an oil phase material or an oil shell having at least one aqueous simple emulsion droplet is provided, a homogeneous step is performed for the solution system. The homogenization step is as described above, and is a step of providing an external force in the mixed solution to uniformly distribute the oil phase to the continuous aqueous phase solution. For example, the homogenization step can be performed by high speed and smooth rotation of the rotor in a solution to form a high frequency, strong circumferential shearing motion, and a strong reciprocating motion through a narrower gap through a stator. For example, a high-frequency, intense circumferential shearing motion can be formed by the high-speed and smooth rotation of the rotor in the solution, and through the action of the stator in the narrow gap to form a reciprocating hydraulic shear, friction, centrifugal extrusion, liquid flow collision and other comprehensive effects, so that the oil phase material is finely shredded to present a stable oil droplet state. Or, the solution is subjected to ultrasonic oscillation, and a vacuum bubbles are rapidly formed in the emulsion and rapidly ruptured, thereby generating a strong shearing force, so that the oil phase material gradually forms an oil droplet state to achieve the stability of the aqueous phase and the oil phase in the emulsion. For the purposes of the foregoing, in a preferred embodiment of the present invention provides, homogenization steps including ultrasonic oscillation, rotor-stator homogenization or extrusion homogenization.

On the other hand, in order to simplify the operation steps thereof, in a preferred embodiment of the present invention, the first aqueous phase solution, the emulsifier and the oil phase material of steps S11, S13 and S15 can be simultaneously added to the solution, and homogenize to form the storage solution. If the first aqueous phase solution, the emulsifier, and the oil phase material are compatible with each other, the mixing order of the mixed solution may not be performed in accordance with steps S11 to S15. The essential components are directly mixed and homogenized, and the form of the continuous aqueous phase coated with the fine oil phase material can be spontaneously formed to give same storage solution obtained by the sequential addition step.

Figure 2:
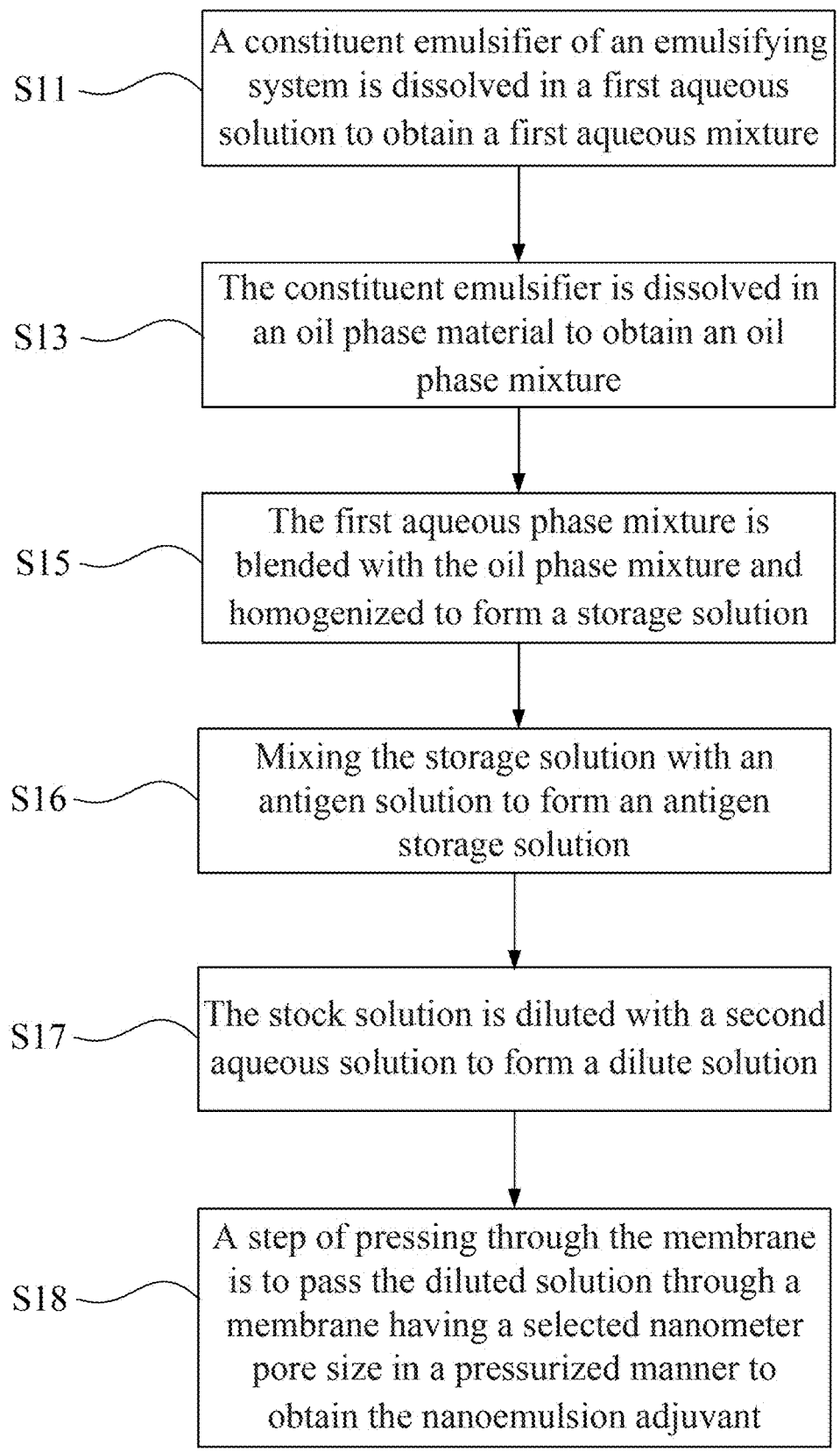
FIG. 2. A flow chart of a method for preparing a nanoemulsion according to another preferred embodiment of the present invention.

Next, regardless of the formation step of the storage solution, in a preferred embodiment of the present invention, as shown in FIG. 2, a step S16 may further be included, which is after the preparation of the storage solution is completed, it is mixed with an antigen solution to form an antigen storage solution. Wherein, the antigen may be hydrophobic or hydrophilic. The antigen within the antigen solution is adsorbed to a continuous aqueous or oil phase material within the storage solution to form the antigen storage solution, which is delivered to the target organism using the emulsion as a carrier.

As described in the above paragraph, the antigen solution does not contain any immunostimulant other than the antigen. The immunostimulant is that induces activation or increases activity of any composition to stimulate immune system. Based on the foregoing principles, the immune stimulant provided by the present invention includes but is not limited to: toll-like receptor (TLR) agonists or short antimicrobial peptides, such as CpG oligodeoxynucleotides (TLR-9), host defense peptides (TLR-4), saponins (TLR-2, TLR-4), monophosphoryl lipid A (TLR-4), flagellin (TLR-5) and antibacterial peptides.

As shown in the step S17, the preparation method of the nanoemulsion adjuvant provided in a preferred embodiment is to dilute the storage solution so as to reduce the density of the microemulsion particles in the emulsion and avoid excessively dense micro-emulsion particles passing through the membrane pores at the same time, resulting in clogging. On the other hand, by diluting the storage solution, the pressure caused when the storage solution passes through the membrane can be effectively reduced, and the membrane can be prevented from being broken due to excessive pressure.

As shown in step S18, the nanoemulsion adjuvant provided in a preferred embodiment is prepared by passing the diluted solution obtained in the previous step through a membrane with nanopores of a specific size by applying external pressure. The oil droplets of the oil phase in the dilute solution are passed through the nanopores of the membrane, and the particle size of the oil droplets is adjusted from micron or submicron down.

In a preferred embodiment, the step of pressing through the membrane is to set the membrane with the specific nanometer pore size in the middle of a bi-directional pressing device, and the both sides of the bi-directional pressing device each have a reserved space to accommodate the diluted solution. After the diluted solution passes through the membrane from one side of the bidirectional pressing device to the other side by external pressure, the diluted solution can be pressed from the other side through the membrane to the original side. By this means, less emulsion was consumed in the step of passing through membrane, and the frequency of replacing the operating device is reduced, so the preparation of the nanoemulsion adjuvant can be completed in less time and more efficiently.

As described in the paragraph above, in another preferred embodiment of the present invention, the bi-directional pressing device is a standard extruder used for preparing a liposome, and comprises a membrane support device at the center and is connected to two hallow columns on the left and right sides. The hollow columns have an internal space for accommodating the diluted solution, and each has a push rod that closely fits the inner wall of the hollow column. When the push rods are pushed in the direction of the membrane support device, the diluted solution can be passed through the membrane support device to the internal accommodating space of the other hollow column, then the push rod of the hollow column on the other side can be pressed to return the solution to the internal accommodating space of the original hollow column. Wherein, the membrane support device comprise: a outer sleeve of the extruder, at least one membrane support, a membrane, a bearing and a clamp nut, wherein the components have an internal cavity and communicate with the hollow tubular columns on both sides. Each of these elements has an internal cavity and communicates with the internal accommodating space of the hollow columns on both sides so that the diluted solution can smoothly pass through the membrane.

In another preferred embodiment of the present invention, the step of pressing through the membrane back-and-forth may be repeated at least once until the particle size of the microemulsion particles in the dilute solution is consistent with the pore size of the membrane and the distribution of the particles of the microemulsion particles is uniform. The particle size distribution of the nanoemulsion adjuvant obtained in this step is more uniform than the microemulsion generally obtained only through extrusion or homogenization. Therefore, when used as a carrier for drug delivery, it can be more evenly distributed in the administration section to improve the efficiency of administration. In particular, when the nasal cavity is used as a route of administration, it can be more evenly dispersed in the microvessels in the nasal cavity to achieve better administration efficiency. When used as a vaccine carrier, the nano-sized emulsion particles obtained through the repeated steps can provide better biological activity, trigger a stronger immune stimulatory response, and enhance the efficacy of the vaccine.

Figure 3:
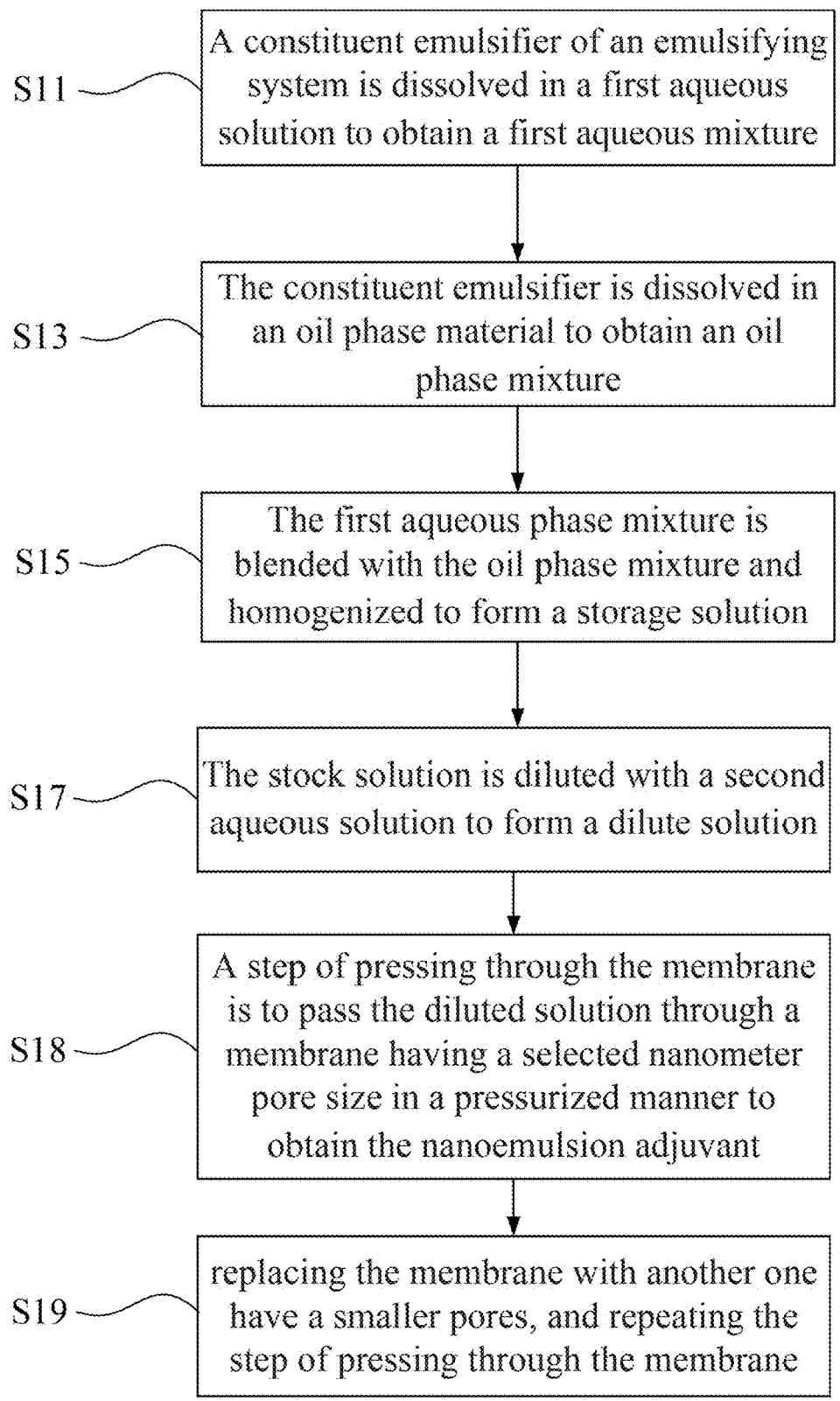
FIG. 3. A flow chart of a method for preparing a nanoemulsion according to another preferred embodiment of the present invention.

As described in the above paragraph, the step of pressing back and forth through the membrane may be repeated several times. As shown in FIG. 3, a step S19 may further be included following the step of pressing through the membrane. S19 is a step of replacing the membrane with another one have a smaller pores, and repeating the step of pressing through the membrane.

Wherein, the pore size of the membrane to be replaced in this step may be more than one, and the membrane replacement may be performed sequentially according to the decreasing of the pore size. The advantage of this operation step is to avoid that the microemulsion particles in the emulsion are too large to smoothly pass through the membrane with smaller pore, even causing clogging. Through this step, after the microemulsion particles are uniformly miniaturized to a smaller particle size, the next size level of uniform miniaturization can be performed, and the homogeneity of the microemulsion particles can be ensured in the process of sequential miniaturization, avoiding some of the micro-emulsion particles pass through the membrane and some fail, resulting in an excessively large particle size distribution. This will result in a decrease in the efficiency of the nanoemulsion adjuvant as a carrier for drug delivery, affecting the effectiveness and the distribution of the pharmaceutical agent.

In the following, the technical contents, features, and achievements of the present invention will be described with specific implementation examples and can be implemented accordingly. However, the scope of protection of the present invention is not limited thereto.

Example 1

Preparation of Nano-Scale PELC Emulsion (nanoPELC) and Nano-Scale SLACL Emulsion (nanoSLACL)

Preparation of a PEGylated-polyester: PEG-b-PLACL was synthesized by the ring-opening polymerization of lactide and ε-caprolactone in the presence of polyethylene glycol 5,000 monomethyl ether (MePEG$_{5000}$) and Tin(II) 2-ethylhexanoate (SnOct$_2$). Briefly, a predetermined amount of MePEG$_{5000}$ (2.1 g), lactide (0.58 g), and ε-caprolactone (0.47 g) was placed into a polymerization ampoule. The mixture was further degassed and sealed under vacuum. Polymerization was carried out in bulk under vacuum at 140° C. for 24 h. The copolymer was dissolved in acetone and then poured into ethanol. The precipitated polymer was finally collected by filtration and dried in vacuo to yield the pure product.

Preparation of a sorbitan-polyester: Sorbitan-polyester copolymers were synthesized by a two-stage method. First, a predetermined amount of sorbitol was added to the flask. Sorbitan was prepared simply by distilling water out of sorbitol at 180° C. for 2 h in the presence of phosphoric acid, using a Rotavapor® R-210 (Buchi Labortechnik AG, Switzerland) under vacuum. In the second stage, the sorbitan-polyester copolymer was synthesized by ring-opening polymerization of DL-lactide and ε-caprolactone in the presence of sorbitan and SnOct$_2$ at 140° C. for 24 h. The resulting sorbitan-poly(lactide-co-ε-caprolactone) copolymer (named sorbitan-PLACL) was dissolved in 100 ml of dichloromethane, and then the solution was washed with 50 ml of distilled water. The solvent of the organic phase was partially evaporated under reduced pressure.

For PELC preparation, 120 mg of PEG-b-PLACL, 0.8 mL of PBS, and 1.1 mL of an oily solution consisting of squalene and Span® 85 (85/15 v/v) were emulsified using a homogeniser at 6 000 rpm for 5 min. Span® 85 was replaced by the same amount of sorbitan-PLACL so as to yield SLACL emulsion.

Next, the micron-sized PELC and the SLACL emulsions were 1000× diluted in PBS and the size of diluted emulsions was controlled by sequentially extruding through polycarbonate membrane filters with a pore size of 1000, 400, 200 and 100 nm. When the diluted solution passes through the membrane from one side of the bi-directional pressing device to the other side, the dilute solution is then pressed from the other side through the film to the original side and back-and-forth 11 times to obtain the nano scale PELC or the nano scale SLACL emulsions. The size distribution and mean number of emulsion particles was determined by the laser light scattering.

Figure 4A:
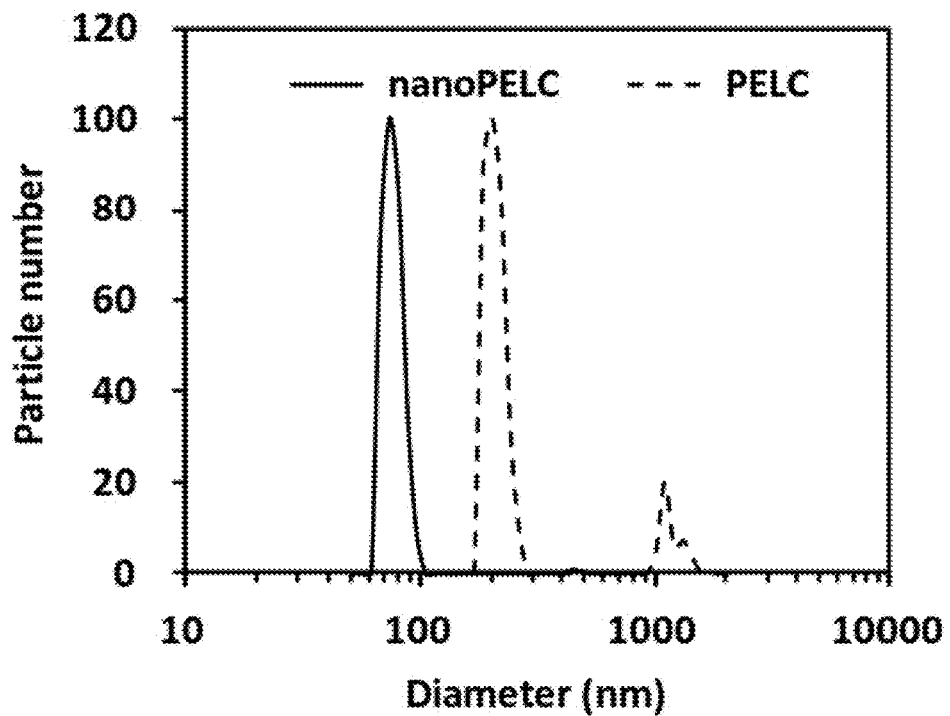
FIGS. 4A and 4B. The particle size distribution of nano scale PELC emulsion (nanoPELC) and nano scale SLACL emulsion (nanoSLACL) in a preferred embodiment of the present invention.
Figure 4B:
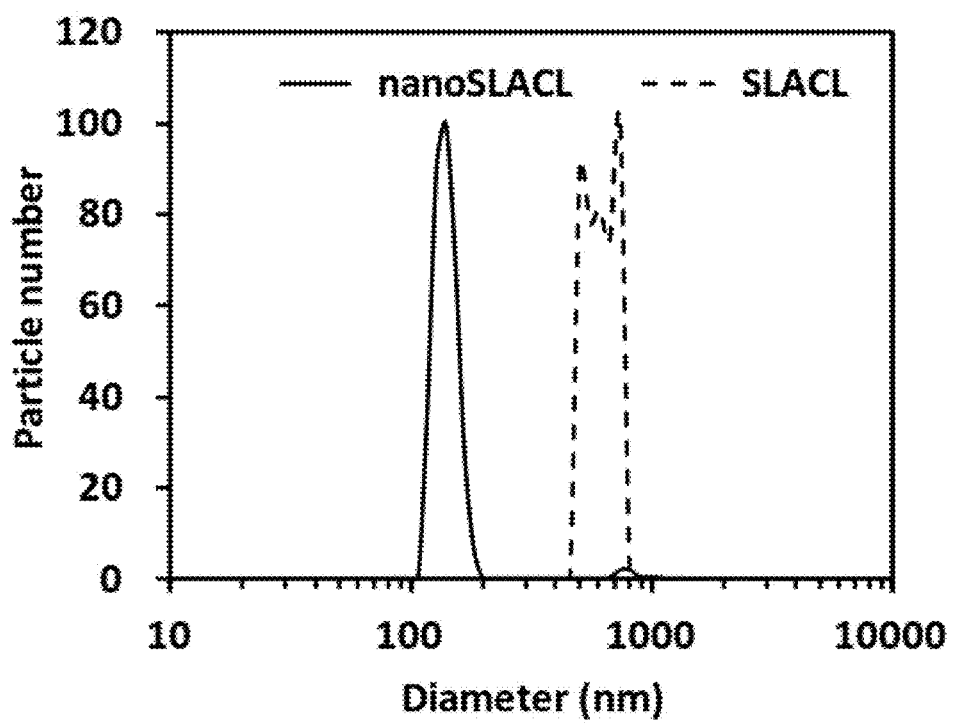
Figure 5A:
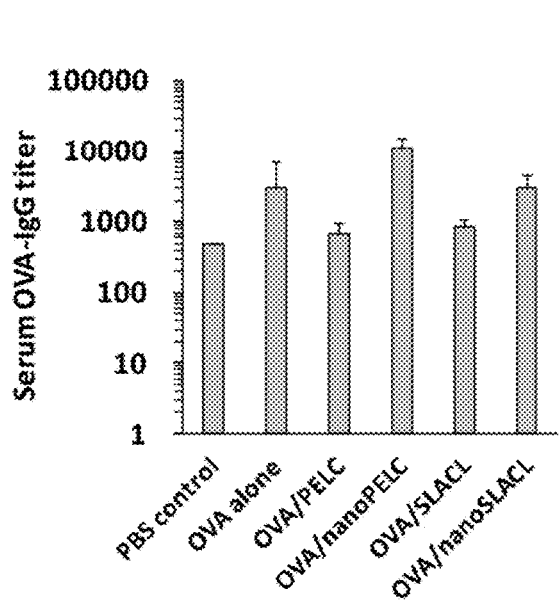
FIG. 5A to 5C. Immune response results of intranasal mucosa and systemic B-cells using a nanoemulsion as a vaccine adjuvant for intranasal administration in a preferred embodiment of the present invention.
Figure 5B:
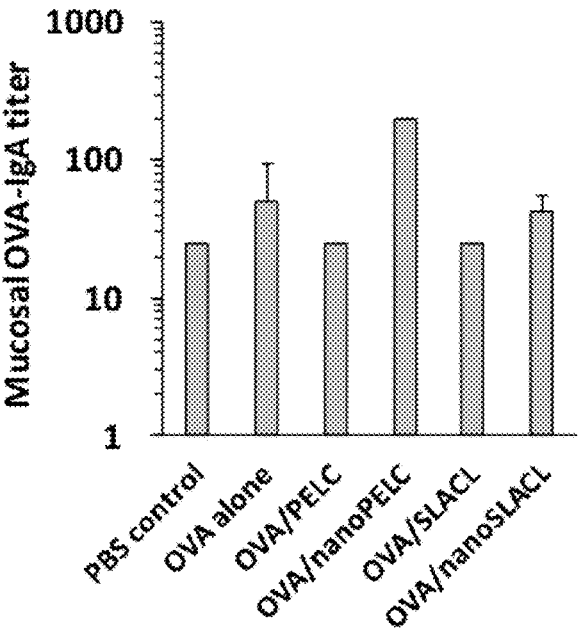

As shown in FIGS. 4A and 4B, it can be observed that the nanoscale PELC emulsion (nanoPELC) has a particle size of less than 200 nm (FIG. 5A), whereas the size of the non-nano PELC emulsion particles are mostly distributed between 200 nm and 300 nm (FIG. 5B). On the other hand, the nano-scale SLACL emulsion (nanoSLACL) has a particle size ranging from 100 nm to 200 nm, while the non-nano SLACL emulsions are mostly distributed between 450 nm and 1000 nm. It can be seen that both the PELC and SLACL emulsion particles via the nanosized process are effective in miniaturizing the particle size and conforming to the definition of the nano-scale.

Example 2

Immune Response Results of B-Cells Using a Nanoemulsion as a Vaccine Adjuvant for Intranasal Administration 6-week old female BALB/c mice were divided into 6 groups: vaccinated with PBS, ovalbumin (OVA alone), OVA adjuvanted with 10% PELC, OVA adjuvanted with 10% nanoPELC, OVA adjuvanted with 10% SLACL, and OVA adjuvanted with 10% nanoSLACL. Mice (n=3-6 per group) were intranasally vaccinated with PBS or OVA formulation (100 μg/dose) once a week for 3 weeks. One week after the final vaccination, the mice were sacrificed to collect serum, nasal washes for determination of the titers of OVA-specific IgG, IgE and IgA by ELISA (enzyme-linked immunosorbent assay).

Figure 5C:
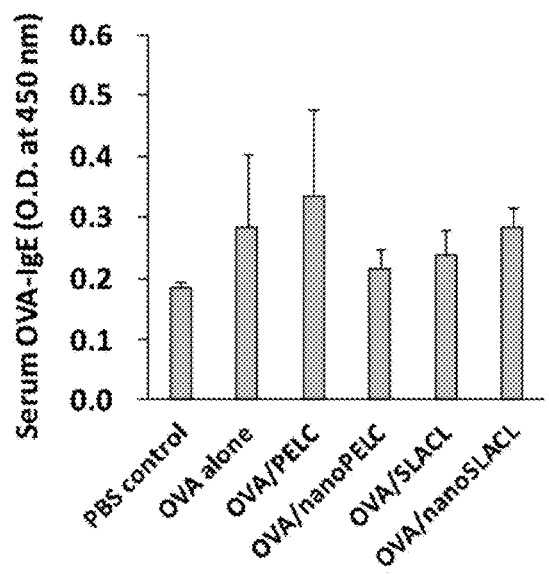

First, the results of detection of OVA-specific IgG, IgE, and IgA concentrations in mouse serum and nasal washings are shown in FIGS. 5A to 5C. It can be found in the group of mice immunized with ovalbumin loaded via nanoscale PELC emulsion (OVA/nanoPELC) and nanoscale SLACL emulsion (OVA/nanoSLACL), whose ovalbumin-specific IgG and IgA levels in the serum and ovalbumin-specific IgA levels in the nasal mucosa were higher than in the PBS control group. It is evident that these emulsions can indeed deliver ovalbumin. In addition, the delivery efficiency of ovalbumin via nanoscale PELC emulsion (OVA/nanoPELC) was significantly better than that of ovalbumin alone (OVA alone). On the other hand, nano-scale PELC emulsion and SLACL emulsion have higher delivery efficiency than micron-scale PELC emulsion and SLACL emulsion. Based on the above results, it can be observed that the antigen adjuvanted with the nanoemulsion can effectively induce mucosal and systemic antigen-specific immune responses via intranasal administration. The effect is significantly better than vaccine antigens without adjuvant or submicron scale emulsion.

Example 3

T Cell Immune Response Results Using the Nanoemulsion Adjuvant as a Vaccine Carrier for Intranasal Administration 6-week old female BALB/c mice were divided into 6 groups: vaccinated with PBS, ovalbumin (OVA alone), OVA adjuvanted with 10% PELC, OVA adjuvanted with 10% nanoPELC, OVA adjuvanted with 10% SLACL, and OVA adjuvanted with 10% nanoSLACL. Mice (n=3-6 per group) were intranasally vaccinated with PBS or OVA formulation (100 g/dose) once a week for 3 weeks. One week after the final vaccination, the mice were sacrificed to collect spleen samples for preparing splenocytes suspensions. Splenocytes suspensions were then stained with anti-CD4, anti-CD8 and anti-CD107a antibodies for the measurement of cytotoxic lymphocytes (CTLs) activation by flow cytometric analysis. Splenocytes suspensions ($5\times10_6$ cells/mL) were cultured in the absence or presence of OVA (10 g/mL) for 72 h, and the MTT assay was applied to determine antigen-stimulation index. To determine transcription factors mRNA and cytokines expression, splenocytes suspensions ($5\times10^6$ cells/mL) were cultured in the presence of OVA (10 g/mL) for 24 or 72 h, and the cell pellets and supernatant were collected for total RNA extraction and cytokines measurement, respectively.

Figure 6A:
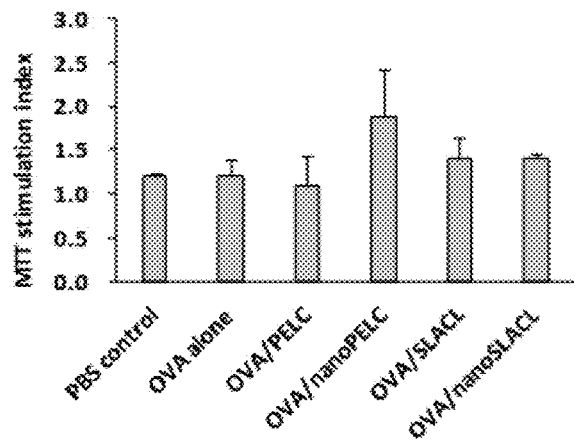
FIG. 6A to 6F. T cell immune profile using a nanoemulsion as a vaccine adjuvant for intranasal administration in a preferred embodiment of the present invention.
Figure 6B:
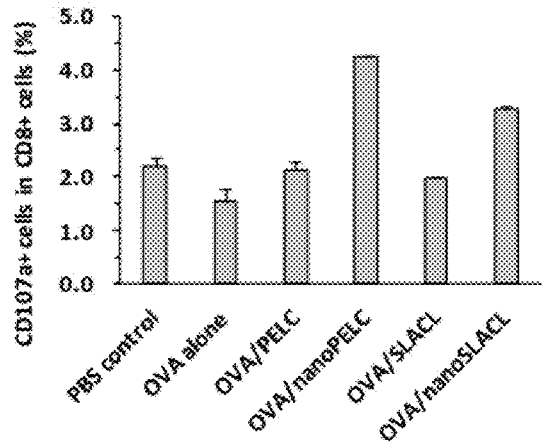
Figure 6C:
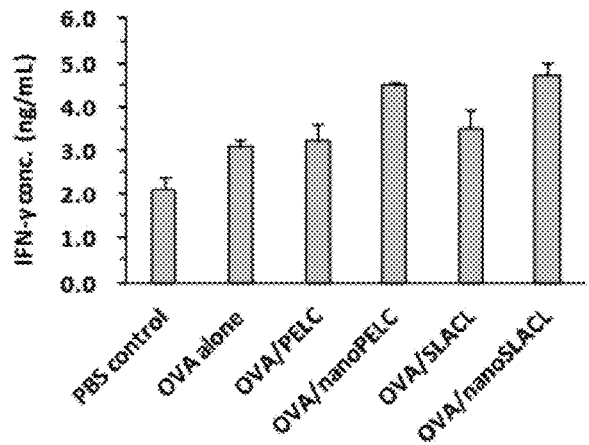
Figure 6D:
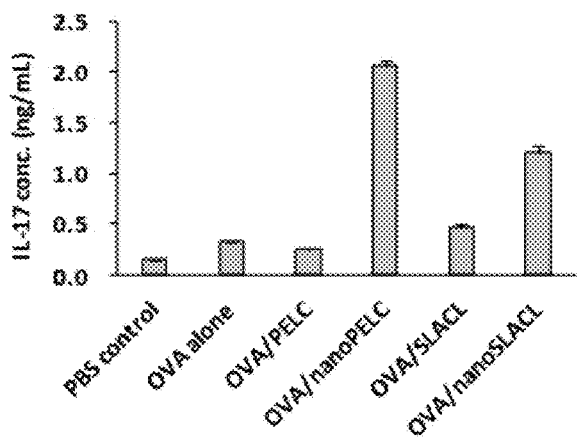
Figure 6E:
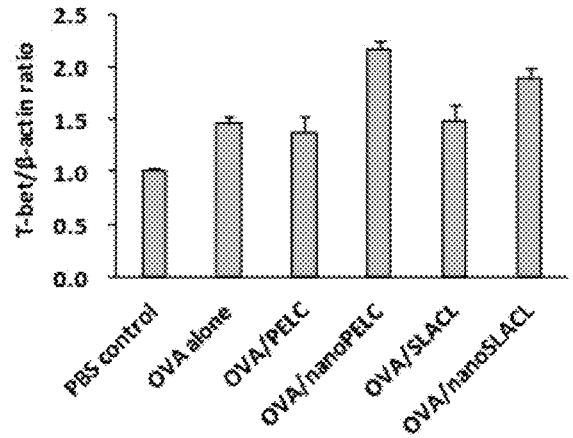
Figure 6F:
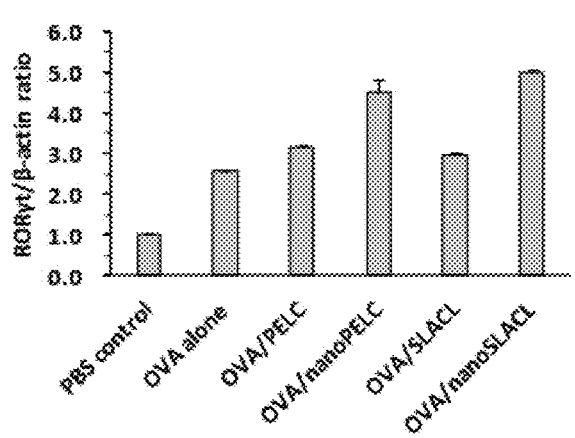

The experimental results are shown in FIGS. 6A to 6F. Antigen-stimulation Index of pancreatic cells in mice immunized with ovalbumin loaded with nanoscale PELC emulsion (OVA/nanoPELC) and nanoscale SLACL emulsion (OVA/nanoSLACL) are higher than other groups (as shown in FIG. 7A). The above phenomenon is more obviously observed in the cytotoxic lymphocytes (CTLs) activation. In the activity assay of cytotoxic T cells, the above phenomenon is more clearly observed. By examining the surface marker CD 8 and the degranulation marker CD107a on the surface of spleen cells, it can be found that the ovalbumin carried by nano-scale PELC emulsion (OVA/nanoPELC) and nano-scale SLACL emulsion (OVA/nanoSLACL) can induce more T cell responses than the general delivery vehicle (as shown in FIG. 7B). Moreover, the activation of these cytotoxic T cells also increased the secretion of cytokines (as shown in FIG. 6C and FIG. 6D), and secreted interleukin-17 and interferon-γ to produce a corresponding immune response. On the other hand, T cell immune response related cells were stimulated with ovalbumin loaded on nanoscale PELC emulsion (OVA/nanoPELC) or nanoscale SLACL emulsion (OVA/nanoSLACL), and T-bet RNA related to interferon-gamma and antigen-specific T cell activation and RORyt RNA related to CD8 cell immune response were found to exhibit higher RNA expression (FIGS. 6E and 6F). This further demonstrated that nanoscale PELC emulsions and nanoscale SLACL emulsions were used as intranasal vaccine carriers to modulate T cell immune responses.

Example 4

Immune Response Results Using the Nanoemulsion Adjuvant as a Melanoma Vaccine Carrier for Intranasal Administration.

6-week old female C57BL/6 mice were intravascularly inoculated with B16-F10/OVA cells (melanoma cells expressing OVA epitopes, $5\times10^5$ cells/mouse). One week later, mice were divided into 4 groups (n=6 per group): vaccinated with PBS, ovalbumin (OVA), OVA adjuvanted with 0.1% PELC and OVA adjuvanted with nanoPELC. The mice were intranasally vaccinated with PBS or OVA formulation (100 μg/dose) once a week for 3 weeks. One week after the final vaccination, some of the mice were sacrificed, and the lung was isolated for pathological observation.

Figure 7:
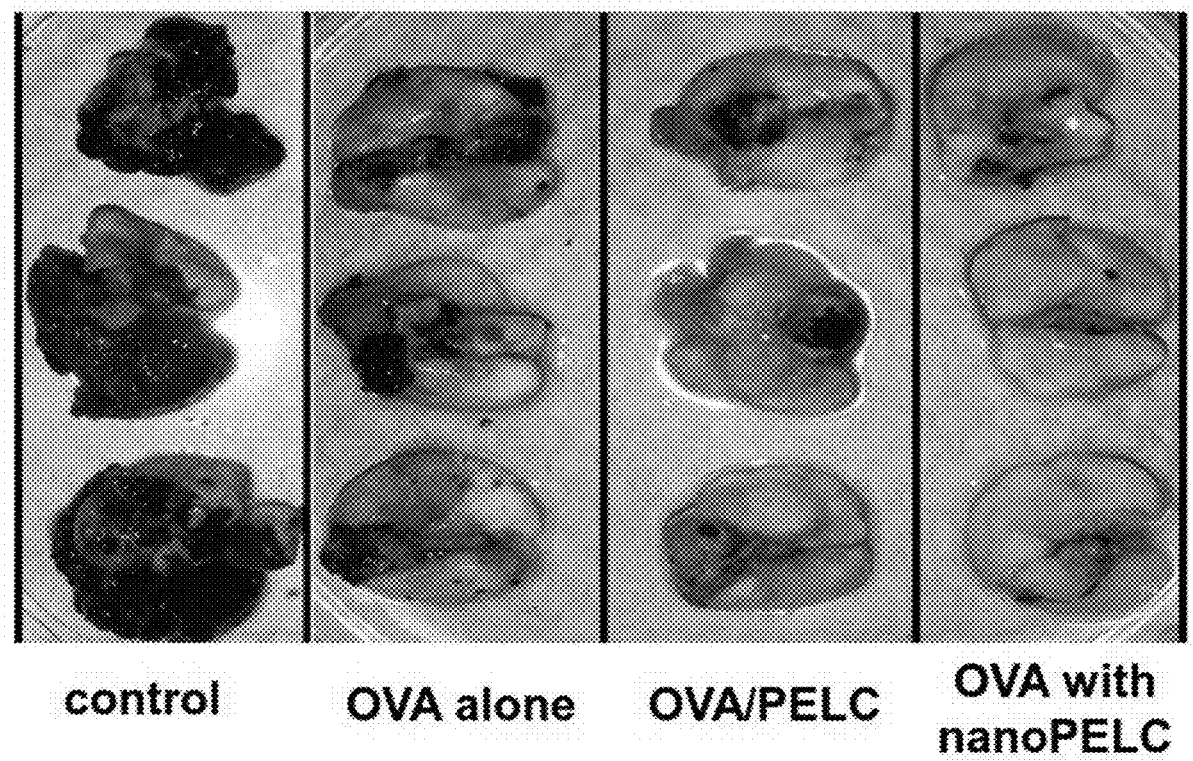
FIG. 7. Lung metastasis of intranasal vaccination with melanoma vaccine adjuvanted with nanoemulsions in a preferred embodiment of the present invention.

The results of the experiment are shown in FIG. 7, in which the pathologically observed lung color of the group given only PBS was the darkest, indicating that it was the most severely infected with the melanoma cell line. The results of the experiment are shown in FIG. 7. In the group administered with PBS only, the pathologically observed lung color was the darkest, indicating that it was most severely infected with melanoma. Followed by the OVA-only group, the melanoma-infected area was not as serious as the PBS group, but it still had a certain area. In the group of OVA adjuvanted with 0.1% micron PELC emulsion, there was still a partial melanoma infection area, but the area was smaller than that of the group directly administered with OVA, indicating that administration in the emulsion dosage form enhanced its biological activity. Lastly, the OVA was adjuvanted with a 0.1% nanoscale PELC emulsion. As shown in the figure, mice had almost no areas of melanoma infection in the lungs, demonstrating that the effectiveness of the nanoemulsion was significantly greater than that of a conventional emulsion.

In summary, the present invention provides a nanoemulsion adjuvant by an effective procedure, which not only has a smaller particle size of the microemulsion particles than the existing emulsion, but also can more effectively uniformize the size of the microemulsion particles. By providing such emulsions with smaller and uniform particle size of the microemulsion particles, the dispersion capability of the emulsion can be effectively improved, especially when the nanoemulsion adjuvant is used in a delivery system for nasal delivery. It can be more effectively dispersed in the microvessels of the nasal cavity and increase the efficiency of drug administration. On the other hand, such a nanoemulsion adjuvant can also be loaded with an antigen or other immune stimulator as a carrier for the vaccine. In the same manner as the nasal cavity as a vaccine delivery route, it was observed through animal models that the vaccine using the nanoemulsion adjuvant as a carrier can effectively induce the B-cell and T-cell immune system response corresponding to the antigen, and can also be used as a cancer vaccine to effectively reduce the occurrence of cancer. Finally, through comparison of the effectiveness of sub-micron and nanoemulsions as vaccine carriers, it was found that the oil phase material of the nanoemulsion exhibit immune stimuli that are difficult to achieve at the submicron level, and biological activity can be effectively improved. Therefore, the nanoemulsion adjuvant and the preparation method thereof provided by the present invention disclose a nanoemulsion adjuvant having a smaller and more uniform particle size, contributing an immune adjuvant that elicited immune response effectively without adverse effects on the human body.

However, the above description is only some preferred embodiments of the present invention and is not intended to limit the scope of the present invention. Any changes and modifications in the shapes, structures, features, and spirits mentioned in the scope of the patent application shall be included in the scope of the patent application for this work.

The invention claimed is:
1. A nanoemulsion adjuvant, which is administered via the nasal mucosa with antigen for increasing the antigen valence, comprising:
 a continuous water phase containing $H_2O$ molecules;
 an oil phase containing metabolizable oil; and
 an emulsion system for stabilizing an interface between the continuous water phase and the oil phase, the emulsion system comprising at least one non-ionic emulsifier;
 wherein the particle size distribution of the microparticles in the nanoemulsion adjuvant is between 20-200 nm;
 wherein the emulsifier is a sorbitan-poly(lactide-co-ε-caprolactone) copolymer.

2. The nanoemulsion adjuvant according to claim 1, wherein nanoemulsion adjuvant comprises:
 the continuous water phase in a weight percentage concentration range of more than 99%;
 the oil phase in a weight percentage concentration range of less than 1%; and
 the emulsion system in a weight percentage concentration range of 0.01% to 0.2%.

3. The nanoemulsion adjuvant according to claim 1, wherein the nanoemulsion adjuvant contains no immunostimulatory agent, said immunostimulatory agent is a TLR agonist, a short-chain antimicrobial peptide or a combination thereof.

4. The nanoemulsion adjuvant according to claim 3, wherein the TLR agonist is a CpG oligodeoxynucleotide (TLR-9), a saponin (TLR-2, TLR-4), monophosphoryl lipid A (TLR-4), a flagellin (TLR-5), or a combination thereof.

5. The nanoemulsion adjuvant according to claim 1, wherein the emulsion system contains no cationic emulsifier, said cationic emulsifier is a cetylpyridinium halide, a cetylpyridinium chloride, a cetyltrimethylammonium halide, a cetyldimethylethylammonium halide, a cetyltibutylammonium halide, a dodecyltrimethylammonium halide, a myristyltrimethylammonium halide or a combination thereof.

6. The nanoemulsion adjuvant according to claim 1, wherein the continuous water phase is a pure water solution, a phosphate solution, a citrate solution, a carbonate solution, a bicarbonate solution, a potassium chloride solution, a sodium chloride solution, a glucose solution, a lactate Ringer's solution or a combination thereof.

7. The nanoemulsion adjuvant according to claim 1, wherein the oil phase is a metabolizable oil, a fatty acid or a combination thereof.

8. The nanoemulsion adjuvant according to claim 7, wherein the metabolizable oil is an animal oils, a vegetable oils, a natural oils, a synthetic oils, a semi-synthetic derivatives or a combination thereof.

9. A method of preparing a nanoemulsion adjuvant which is administered via the nasal mucosa with antigen for increasing the antigen valence, comprising the steps of:
 dissolving a constituent emulsifier of an emulsion system in a first aqueous solution to obtain a first aqueous mixture;
 dissolving the constituent emulsifier in an oil phase to obtain an oil phase mixture;
 mixing and homogenizing the first aqueous mixture and the oil phase to obtain a stock solution;
 diluting the stock solution with a second aqueous solution to form a dilute solution; and
 pressurizing the dilute solution through a membrane having a selected nanometer pore size to obtain a nanoscale emulsion adjuvant as according to claim 1.

10. The method of preparing a nanoemulsion adjuvant according to claim 9, wherein the pressurizing step is arranging the membrane in the middle of a bi-directional pressing device to divide the device into two sides, wherein the diluting solution is pressed from the one side of the bi-directional pressing device through the membrane to the other side, the dilute solution can then be pressed from the other side of the bi-directional pressing device through the membrane to the original side to complete the step of pressing back and forth.

11. The method of preparing a nanoemulsion adjuvant according to claim 9, further comprising a step after the pressurizing step which the membrane is replaced with a membrane having smaller pore diameter, and the repetition is performed after that.

12. The method of preparing a nanoemulsion adjuvant according to claim 10, wherein the pressurizing step is back and forth repeated at least once until the particle size of the emulsion particles in the diluted solution matches the pore size of the membrane and the particle size distribution is uniform.

13. The method of preparing a nanoemulsion adjuvant according to claim 10, wherein the bi-directional pressing device is a standard extruder for preparing liposomes.

\* \* \* \* \*